United States Patent [19]

Lienhop et al.

[11] Patent Number: 5,730,997
[45] Date of Patent: Mar. 24, 1998

[54] TASTEMASKED LIQUID PHARMACEUTICAL DELIVERY SYSTEM

[75] Inventors: Keith S. Lienhop, St. Charles, Mo.; Robert C. Cuca, Edwardsville, Ill.; Thomas Charles Riley, Jr., Ballwin; R. Saul Levinson, Chesterfield, both of Mo.

[73] Assignee: KV Pharmaceutical Company, St. Louis, Mo.

[21] Appl. No.: 712,436

[22] Filed: Sep. 11, 1996

Related U.S. Application Data

[63] Continuation of Ser. No. 282,495, Aug. 1, 1994, abandoned.

[51] Int. Cl.$^6$ ........................................... A61K 47/10
[52] U.S. Cl. .................. 424/439; 424/485; 424/486; 514/974; 514/849; 514/850
[58] Field of Search .................. 424/439, 485, 424/486; 514/974, 849, 850

[56] References Cited

U.S. PATENT DOCUMENTS

| | | | |
|---|---|---|---|
| 4,381,318 | 4/1983 | Lynch | 426/658 |
| 4,448,778 | 5/1984 | Lynch | 424/260 |
| 4,471,001 | 9/1984 | Lynch | 426/573 |
| 4,534,960 | 8/1985 | Chavkin | 424/49 |
| 4,959,225 | 9/1990 | Wong et al. | 426/3 |
| 4,963,359 | 10/1990 | Haslwanter et al. | 424/440 |
| 4,971,798 | 11/1990 | Coia et al. | 424/440 |
| 4,994,260 | 2/1991 | Kallstrand et al. | 424/10 |
| 4,996,222 | 2/1991 | Carlin et al. | 514/400 |
| 5,013,716 | 5/1991 | Cherukuri et al. | 514/23 |
| 5,028,632 | 7/1991 | Fuisz | 514/772 |
| 5,049,568 | 9/1991 | Kristuf et al. | 514/317 |
| 5,202,129 | 4/1993 | Samejima et al. | 424/489 |
| 5,272,137 | 12/1993 | Blase et al. | 514/54 |
| 5,288,479 | 2/1994 | Gorman et al. | 424/401 |
| 5,368,852 | 11/1994 | Umemoto et al. | 424/78.1 |
| 5,409,907 | 4/1995 | Blase et al. | 514/54 |
| 5,424,418 | 6/1995 | Duflot | 536/103 |
| 5,436,329 | 7/1995 | Caboche | 536/103 |

OTHER PUBLICATIONS

Ackroff et al. Physiol. Behav 49(6)1047–1060 Jun. 1991.
Lanthier et al. GUT 26/4:415–420 (1985).
Desimone et al J. Gen. Physiol. 83(5): 633–656 May 1984.
Ho J. Pharm. Sci. 73(5): 600–603 may 1984.
Sclafani et al Neurosci Bio Behar. Rev. 11(2): 173–180 (1987).
Simon et al. Chem. Senses. 15(1):1–23 (1990).
Toufeili et al Food Chem. 47(1):17–22 (1993).
Lichtenthaler Dtsch. Zahnagrtziz. 2, 37(1): 46–49 (1982).
Simon et al Am. J. Physiol. 251(3) R598–R608 1986.
Lee et al Food Chem. 2(2):95–105 1977.
Noma et al Kumamoto Med J. 24(1):1–9 1971.

*Primary Examiner*—Neil S. Levy
*Attorney, Agent, or Firm*—Gary M. Nath; Nath & Associates

[57] ABSTRACT

A substantially tasteless liquid phramaceutical delivery system containing an active material and a high osmolarity aqueous system comprising (i) water; (ii) about 20% to about 45% by weight sugar derivative; (iii) about 10% to about 15% by weight hydrogenated maltose syrup; and (iv) about 0% to about 35% by weight polyhydroxy alcohol.

22 Claims, No Drawings

1

TASTEMASKED LIQUID PHARMACEUTICAL DELIVERY SYSTEM

This application is a Continuation of U.S. patent application Ser. No. 08/282,495, filed Aug. 1, 1994 now abandoned, the entire contents of which are hereby incorporated in their entirety.

BACKGROUND OF THE INVENTION

1. Field of the Invention

This invention relates to substantially tastemasked liquid pharmaceutical delivery systems and to methods for making the same. More particularly, the invention relates to tastemasking the noxious, bitter tastes associated with bad tasting drugs for use in a liquid delivery systems to prepare pleasant tasting orally administered compositions.

2. Description of the Prior Art

Oral pharmaceutical formulations are administered to patients in many forms, such as liquid solutions, emulsions or suspensions, as well as in solid forms such as capsules or tablets. Preparations administered in tablet or capsule form are usually intended to be swallowed whole. Therefore, the often disagreeable taste of the active ingredient need not be taken into account in formulating the medicine, except as a means to prevent the taste from being apparent during the short time that the medicine is in the mouth. Such means may include forming the active into a matrix preparation, the use of capsules or simply compressing a tablet firmly so that it will not begin to disintegrate during the short time that it is intended to be in the mouth.

In some preparations, the unpleasant tasting particles are coated with water-soluble and/or water-insoluble coating agents, film forming polymers, water-swelling agents and acid soluble agents.

In contrast, liquid preparations or preparations in the form of solutions or suspensions are used to tastemask bitter tasting drugs by use of sucrose sweetening agents and/or flavoring agents. These formulations are advantageous for administration to children and the elderly. Such formulations have high patient compliance and are easily taken. Such formulations are generally prepared using an organic solvent system and may even contain high amounts of ethyl alcohol, i.e., around 8%. Some of the foregoing procedures are described in the following patents.

U.S. Pat. No. 2,954,322 to Heilig, et al. discloses a tablet intended for oral administration wherein the whole tablet is coated with a mixture of shellac and polyvinylpyrrolidone. It is intended that the tablet be swallowed whole and that the coating will disintegrate in the stomach to release the active medicament.

U.S. Pat. No. 3,133,863 to Tansey, et al. discloses a method for forming granules of medicament that can be compressed into tablet form, wherein the granules include various polymers dispersed throughout the granules. One embodiment comprises acetaminophen mixed with PVP and methyl cellulose.

U.S. Pat. No. 3,420,931 to Daum, et al. discloses sugar-coated pharmaceutical preparations ("Dragees") coated with a mixture of sugar and a vinyl polymer such as PVP. The coating may also contain cellulose derivatives.

U.S. Pat. No. 3,458,622 to Hill discloses a controlled release tablet wherein the active medicament is contained in a core comprising a matrix of a mixture of PVP and a carboxyvinyl (polyacrylic acid) hydrophilic polymer.

U.S. Pat. No. 4,252,786 to Weiss, et al. discloses a controlled release tablet similar to that of Hill, wherein the core containing the active medicament is coated with a relatively insoluble, water permeable, rupturable film comprising a combination of hydrophobic and hydrophilic polymers. Cellulose acetate is disclosed as one of the hydrophobic polymers. The tablets of Weiss, et al. and Hill are intended to be swallowed whole.

U.S. Pat. No. 4,415,547 to Yu, et al. discloses sustained release pharmaceutical tablets consisting essentially of drug pellets encapsulated with a water-soluble film-forming substance and a water-insoluble film-forming substance. The materials are blended and compressed into tablet form with a compressible tableting mixture.

U.S. Pat. No. 4,059,416 to Cherukuri, et al. discloses a process for preparing a zinc compound delivery system comprised of a zinc core material coated with a first hydrophilic coating comprising a hydrocolloid material and a second hydrophobic coating selected from the group consisting of fats, waxes and mixtures thereof. The delivery system masks the bitter flavor characteristic of zinc compounds.

U.S. Pat. No. 5,085,868 to Mattsson, et al. discloses a liquid dosage form for oral administration of a pharmaceutically active substance characterized in that it includes an encapsulated or embedded pharmaceutically active substance in a pharmaceutically acceptable non-aqueous liquid. More particularly Mattsson, et al. provide a liquid delivery system for active compounds which have an unpleasant taste which prevents the active compound from degrading in the liquid medium. The mechanism behind this phenomenon is described as first the application of a liquid carrier in which the active compound is not soluble or soluble to a very low extent and secondly the fact that the active compound is microencapsulated or embedded in a micromatrix structure to delay release of the active compound from the matrices or microcapsules in an aqueous media. The combination of these two factors is a solid ground for obtaining the above-mentioned properties.

In contrast, U.S. Pat. No. 3,879,511 to Goodhart, et al. discloses use of a vegetable oil vehicle to suspend a coated unpleasant tasting drug. The suspension is alleged to be stable, palatable and therapeutically active.

Unlike the prior art, the present invention is directed to the discovery of an aqueous based liquid delivery system that can be used to orally administer the active component and which achieves a good balance of tastemasking for both water-soluble and water-insoluble active components.

SUMMARY OF THE INVENTION

This invention relates to a substantially tasteless liquid pharmaceutical delivery system, comprising: (a) an active material and (b) a high osmolarity aqueous system comprising: (i) water; (ii) about 20% to about 45% by weight sugar derivative; (iii) about 10% to about 15% by weight hydrogenated maltose syrup; and (iv) about 0% to about 35% by weight polyhydroxy alcohol.

An alternative embodiment involves use of an active material which is a drug selected from the group consisting of analgesics, anti-inflammatories, antihistamines, antitussives, expectorants, decongestants, narcotics, antibiotics, bronchodilators, cardiovasculars, central nervous system drugs, minerals, vitamins, metal salts and mixtures thereof disbursed within the delivery system.

A further embodiment of the invention involves a process for preparing a substantially tasteless liquid pharmaceutical delivery system, comprising a) preparing an aqueous phase containing: (i) water; (ii) about 20% to about 45% by weight sugar derivative; and (iii) about 10% to about 15% by weight hydrogenated maltose syrup; b) blending the aqueous phase to form a high osmolarity homogenous mixture of components; c) adding the active material to water and about 0% to about 35% by weight polyhydroxy alcohol; d) uniformly dispersing the active material within the water to obtain a smooth dispersion or dissolution to form an active phase; and e) blending the aqueous phase a) with the active phase d) to form a substantially tasteless liquid pharmaceutical delivery system and recovering the same.

DETAILED DESCRIPTION OF THE INVENTION

The present invention involves the preparation of a liquid tastemasked system by dispersing the active material in a high osmolarity aqueous solution. In this manner a substantially tasteless liquid pharmaceutical delivery system is formed which comprises: (a) an active material; and (b) a high osmolarity aqueous system comprising: (i) water; (ii) about 20% to about 45% by weight sugar derivative; (iii) about 10% to about 15% by weight hydrogenated maltose syrup; and (iv) about 0% to about 35% by weight polyhydroxy alcohol.

The active materials or drug(s) may be described as a single drug entity or a combination of entities. The term "drug" includes without limitations, medicaments, vitamins, mineral supplements and other chemical or biological substances intended for use in the treatment, prevention, diagnosis, cure or mitigation of disease or illness, or substances which affect the structure or function of the body.

Suitable categories of drugs that may be employed in the instant system may vary widely and generally represent any stable water-soluble or water-insoluble drug compound and combination thereof. Illustrative categories and specific examples include: (a) antitussives, such as dextromethorphan, dextromethorphan hydrobromide, noscapine, carbetapentane citrate and chlophedianol hydrochloride; (b) antihistamines, such as chlorpheniramine maleate, phenindamine tartrate, pyrilamine maleate, doxylamine succinate and phenyltoloxamine citrate; (c) decongestants, such as phenylephrine hydrochloride, phenylpropanolamine hydrochloride, pseudoephedrine hydrochloride, ephedrine; (d) various alkaloids, such as codeine phosphate, codeine sulfate and morphine; (e) mineral supplements such as potassium chloride, zinc chloride and calcium carbonates, magnesium oxide and other alkali metal and alkaline earth metal salts; (f) laxatives, vitamins and antacids; (g) ion exchange resins such as cholestyramine; (h) anti-cholesterolemic and anti-lipid agents; (i) antiarrhythmics such as N-acetylprocainamide; (j) antipyretics and analgesics such as acetaminophen, aspirin and ibuprofen; (k) appetite suppressants such as phenylpropanolamine hydrochloride or caffeine; and (l) expectorants such as guaifenesin.

Additional useful active medicaments include anti-inflammatory substances, coronary dilators, cerebral dilators, peripheral vasodilators, anti-infectives, psychotropics, antimanics, stimulants, laxatives, gastrointestinal sedatives, antidiarrheal preparations, anti-anginal drugs, vasodialators, anti-arrythmics, antihypertensive drugs, vasoconstrictors and migraine treatments, antibiotics, tranquilizers, antipsychotics, antitumor drugs, anticoagulants an antithrombotic drugs, hypnotics, sedatives, antiemetics, anti-nauseants, anti-consulsants, neuromuscular drugs, hyper- and hypo-glycaemic agents, thyroid and antithyroid preparations, diuretics, antispasmodics, uterine relaxants, antiobesity drugs, anabolic drugs, erythropoietic drugs, antiasthmatics, cough suppressants (anti-tussives), mucolytics, anti-uricemic drugs and the like.

Mixtures of the drugs and medicaments may also be used.

Particular unpleasant tasting drugs include pyridonecarboxylic acid antibacterial agents whose degree of unpleasantness is said to be strongest, such as 5-amino-1-cyclopropyl-6,8-difluoro-7-(cis-3,5-dimethyl-1-piperazinyl)-1,4-dihydro-4-(oxoquinoline-3-carboxylic acid, Enoxacin, Pipemidic acid, Ciprofloxacin, Ofloxacin and Pefloxacin; antiepileptic drugs such as zonisamide; macrolide antibiotics such as Erythromycin; beta-lactam antibiotics such as penicillins or cephalosporins; psychotropic drugs such as Chlorpromazine; drugs such as Sulpyrine; and antiulcer drugs such as Cimetidine. An exemplary decongestant is pseudoephedrine hydrochloride and mineral would be zinc salts.

The drugs are used in amounts that are therapeutically effective. While the effective amount of a drug will depend on the drug used, amounts of drug from about 0.01% to about 5% have been easily incorporated into the present system while achieving bitter taste masking. Amounts above about 5% may result in the lose of tasteless properties.

According to the present inventive subject matter, the tastemasking of bitter or unpleasant liquid preparations is accomplished by causing a hyperosmotic condition in the pharmaceutical preparation. In this way, it is believed that when the pharmaceutical preparation is administered orally a temporary condition occurs wherein water moves from the taste receptors on the tongue to the liquid in the mouth. The flow of water in this direction is believed to then impede the diffusion of the bitter or otherwise unpleasant particles contained within the pharmaceutical preparation towards those taste receptors. The resulting effect occurs for a sufficient time to allow passage of the bad tasting materials past the receptors before the perception of bad taste can occur.

It should be pointed out that tastemasking of liquid pharmaceuticals has been historically difficult to accomplish for two major reasons: 1) The bad tasting components are usually in solution, so coating technologies are not applicable; and 2) since the bad tasting components are usually in solution as molecules, rapid diffusion to taste receptors occurs. The present effect of using water flux in the opposite direction from the physiological taste receptors overcomes the difficulty in tastemasking liquid pharmaceutical preparations heretofore observed. It should be noted that the concept of high osmolarity to overcome bad taste can also be applied to dry powder/granule formulations for reconstitution with water.

The present formulation must contain at least two distinct phases which are prepared separately and then blended together. One phase, the aqueous phase, contains the osmolarity modifying agents whereas the other phase, the active phase, contains the active material in solubilizing or suspension amounts of water and optional amounts of an organic solvent and additional osmolarity modifying agents. Each phase is designed to be aqueous based and when combined make up the aqueous system.

The aqueous phase contains three components; water, a sugar derivative and a hydrogenated maltose syrup. The water can be added either directly in the amount desired or is preferably added through solutions of the remaining components. The water is generally present in amounts of about 12% to about 30% and preferably about 15% to about 25% by weight of the final system.

The sugar derivative may be selected from a wide variety of sources and is preferably sorbitol, mannitol, xylitol and mixtures thereof. It is generally employed in amounts of about 25% to about 45% and preferably from about 30% to about 40% by weight of the final system. While other carbohydrate sources may be used in addition to these particular sugar derivatives, such other materials would be generally added for sweetness rather than as an osmolarity modifier. The sugar derivatives are also preferably added in solution form, such as a sorbitol solution which normally contains about 30% water by weight.

Another component of the aqueous phase is a hydrogenated maltose syrup. This component, like the sugar derivative, is used to control the solutions osmolarity. The hydrogenated maltose syrup may be derived from high maltose syrups and generally contains about 25% water by weight. A particularly preferred source is Lycasin®, a sugarless sweetener from Roquette Corporation and described in U.S. Pat. No. 4,279,931.

The hydrogenated maltose syrup is generally added in amounts of about 10% to about 15% by weight and preferably from about 11% to about 14% by weight of the final system.

The aqueous phase is prepared by blending the water, sugar derivative, preferably as a sorbitol solution and hydrogenated maltose syrup together in sufficient amounts until the phase has an osmolarity measurement of from about 1500 to about 5000 and preferably about 2000 to about 4000 mOsm/liter (miliosmoles/liter water).

In addition to the foregoing components the aqueous phase may contain buffers, such as sodium citrate and sodium gluconate to maintain the pH of the system. pH values from about 3.0 to about 8.5 have been found effective in the present delivery systems. Acidifiers, such as citric acid, may also be added when desirable, depending on the drug used, solubility conditions and so forth.

In addition to the aqueous phase the system must contain an active phase which contains the active material (pharmaceutical drug) and a solvent system. The present delivery system is aqueous based, and as such can be easily used with all water-soluble active material. When water-insoluble active materials are to be used in the liquid pharmaceutical delivery systems an optional cosolvent is employed, such as propylene glycol. The propylene glycol must be a non-toxic grade of material and be pharmaceutically acceptable. When a cosolvent system is used, water and propylene glycol are generally employed in amounts of about 1 to 2 parts by weight to about 1 to 1 part by weight, respectively.

The active phase is prepared by simply blending the active material into the water or cosolvent system. Once blended, a homogenous solution or dispersion is formed which can be added to the aqueous phase to form the final product. Optionally, osmolarity modifying agents may be used in the active phase and when used are present in amounts of about 10 to about 3500 mOsm/liter, and preferably about 100 to about 2500 mOsm/liter.

Besides the active phase and the aqueous phase, it is beneficial to employ a preservative phase with the present formulations. Well known preservatives are used for this purpose, such as methyl paraben and propyl paraben, in a solvent system comprising a polyhydroxy alcohol. Preferred polyhydroxy alcohols are propylene glycol or glycerin systems. The solvent, when present, is generally used in amounts up to 35% by weight and preferably about 15% to about 30% by weight of the final system. The preservatives are used in amounts of about 0.01% to about 1.0% by weight and preferably 0.1 to 0.5% by weight of the final system. The preservative phase may be prepared by blending the preservative into the solvent and then blending the resulting solution into a mixture containing the active phase and aqueous phase. The preservative phase may contain osmolarity modifying agents in the amount of about 500 to about 2500 mOsm/liter.

A particularly preferred process for preparing the present formulation comprises: a) preparing an aqueous phase containing: (i) water; (ii) about 20% to about 45% by weight sugar derivative; and (iii) about 10% to about 15% by weight hydrogenated maltose syrup; b) blending the aqueous phase to form a high osmolarity homogenous mixture of components; c) adding the active material to water and about 0% to about 35% by weight polyhydroxy alcohol; d) uniformly dispersing the active material within the water to obtain a smooth dispersion or dissolution to form an active phase; and e) blending the aqueous phase a) with the active phase d) to form a substantially tasteless liquid pharmaceutical delivery system and recovering the same. The final system has an osmolarity measurement of from about 4000 to about 9000 and preferably about 5000 to about 7000 mOsm/liter (miliosmoles/liter water). Osmolarity values below 4000 are not effective to mask the bitter taste of most active material. Amounts above 9000 are too difficult to process as a liquid system.

The delivery system may contain additional ingredients, herein referred to as excipients or additives. Exemplary excipients include well known components, but are not limited to sweetening agents, colorants, surfactants, flavors, fragrances, pH modifiers, bulking agents, acidifiers and mixtures thereof which components may be used in amounts up to about 50% and preferable from about 0.01% to about 25% by weight of the delivery system.

The term "excipients" as used herein means substances and materials generally used in the drug or food industry which do not alter the character and function of the active component of the delivery system.

Flavors which may optionally be added to the delivery system, are those well known in the pharmaceutical art. For example, synthetic flavor oils, and/or oils from plants, leaves, flowers, fruits and so forth, and combinations thereof are useful.

Representative flavor oils include spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth.

The amount of flavoring agent employed is normally a matter of preference subject to such factors as flavor type, base type and strength desired. In general, amounts of about 0.05% to about 5.0% by weight of the final product are useful with amounts of about 0.3% to about 1.5% being preferred and about 0.8% to about 1.2% being most preferred.

The delivery system may contain an additional sweetening agent. Sweetening agents may be selected from a wide range of materials such as water-soluble sweetening agents, water-soluble artificial sweeteners, and dipeptide based sweeteners, including mixtures thereof. Without being limited to particular sweeteners, representative illustrations encompass:

A. Water soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof.

B. Water-soluble artificial sweeteners such as the soluble saccharin salts, i.e., sodium or calcium saccharin salts, cyclamate salts, acesulfam-K and the like, and the free acid form of saccharin.

C. Dipeptide based sweeteners such as L-aspartyl L-phenylalanine methyl ester and materials described in U.S. Pat. No. 3,492,131 and the like.

The excipients are added to the delivery system at anytime during processing. It should be recognized that certain excipients should be added prior to, during or after the active phase is blended into the aqueous phase in order to achieve uniform distribution of the ingredients. Preferably, excipients in liquid form are added before the active phase whereas powdered excipients may be added before or after the active phase is blended into the aqueous phase.

Since tastemasking is a key feature of the invention, use of the inventive liquid systems as a solid system is contemplated, but-not generally preferred. In such solid systems, the product would be taken orally and be expected to be retained in the mouth for significant amounts of time to be solubilized and swallowed. Alternatively, the system may be previously disbursed in water to obtain the desired osmolarity and then swallowed.

The following examples are illustrative of preferred embodiments of the invention and are not to be construed as limiting the invention thereto. All percentages are based on the percent by weight of the delivery system unless otherwise indicated and all totals equal 100% by weight.

EXAMPLE 1

This example describes the production of a tastemasked antihistamine liquid formulation.

The mixture was prepared by the following procedure to include the components listed in Table 1.

Three separate solutions are made then mixed together as follows:

I) Water Sodium Gluconate Sodium Saccharin Citric Acid Color Maltitol Solution Sorbitol Solution II) Propylene Glycol Methylparaben Propylparaben Magnasweet #180

III) Water Diphenhydramine Hydrochloride Propylene Glycol

Solution III would then be added with mixing to Solution I.

Solution II would then be added with mixing to the first mixture.

Flavor would be added last and the product recovered.

This formulation represents 67.5 grams of dissolved material in 100 grams of solution resulting in a high osmolarity formulation of approximately 6500 mOsm/liter.

When the formulation was subjected to a multiple member test panel, the product did not exhibit any bitter taste sensation.

TABLE I

| INGREDIENT | % WEIGHT/WEIGHT |
| --- | --- |
| Diphenhydramine Hydrochloride, USP | 0.2111 |
| Purified Water, USP | 16.4624 |

TABLE I-continued

| INGREDIENT | % WEIGHT/WEIGHT |
| --- | --- |
| Sorbitol Solution, USP | 41.8179 |
| Maltitol Solution | 13.9287 |
| Propylene Glycol, USP | 25.8670 |
| Sodium Gluconate, USP | 0.1857 |
| Citric Acid, USP | 0.2111 |
| Saccharin Sodium, USP | 0.1013 |
| Magnasweet 180 | 0.0422 |
| Methylparaben, NF | 0.0844 |
| Propylparaben, NF | 0.0152 |
| Color | 0.0177 |
| Flavor | 1.0553 |
| | 100.0000 |

EXAMPLE 2

This example describes the production of a taste-masked cough/cold liquid containing a decongestant, cough suppressant and antihistamine. The formation was prepared by the following procedure to include the components listed in Table II.

Make three separate solutions containing the following ingredients:

I) Water Sodium Gluconate Sodium Citrate Sodium Saccharin Citric Acid Color Maltitol Solution Sorbitol Solution II) Propylene Glycol Methylparaben Propylparaben Magnasweet #180

III) Water Pseudoephedrine Hydrochloride Dextromethorphan Hydrobromide Chlorpheniramine Maleate Solution III is then added with mixing to Solution I.

Solution II is then added with mixing to the first mixture.

Flavor is added last and the product recovered.

This formulation represents 66.9 grams of dissolved material in 100 grams of solution resulting in a high osmolarity of approximately 5500 mOsm/liter.

When the formulation was tested by a multiple member test panel, the product did not exhibit any bitter taste sensations.

TABLE II

| INGREDIENT | % WEIGHT/WEIGHT |
| --- | --- |
| Pseudoephedrine Hydrochloride, USP | 0.2451 |
| Dextromethorphan Hydrobromide, USP | 0.1225 |
| Chlorpheniramine Maleate, USP | 0.0163 |
| Purified Water, USP | 12.8624 |
| Sorbitol Solution, USP | 52.7602 |
| Maltitol Sollution | 17.5867 |
| Propylene Glycol, USP | 15.6117 |
| Sodium Gluconate, USP | 0.1634 |
| Citric Acid, USP | 0.1225 |
| Sodium Citrate, USP | 0.0817 |
| Saccharin Sodium, USP | 0.0980 |
| Magnasweet 180 | 0.0817 |
| Methylparaben, NF | 0.0735 |
| Propylparaben, NF | 0.0082 |
| Color | 0.0027 |
| Flavor | 0.1634 |
| | 100.0000 |

The invention being thus described, it will be obvious that the same may be varied in many ways. Such variations are not to be regarded as a departure from the spirit and scope of the invention and all such modifications are intended to be included within the scope of the following claims.

What is claimed is:

1. A cough/cold liquid pharmaceutical delivery system having an osmolarity measurement of about 4000 to about 9000 mOsm/liter, which consists essentially of:
   a) from about 0.01% to about 5% by weight of a bitter tasting active material selected from the group consisting of antitussives, antihistamines, decongestants, expectorants and mixtures thereof; and
   b) a high osmolarity aqueous system having an osmolarity measurement of about 1500 to about 5000 mOsm/liter, consisting essentially of:
      (i) about 12% to about 30% by weight water;
      (ii) about 20% to about 45% by weight sugar derivative selected from the group consisting of sorbitol, mannitol, xylitol and mixtures thereof;
      (iii) about 10% to about 15% by weight hydrogenated maltose syrup; and
      (iv) about 0% to about 35% by weight polyhydroxy alcohol selected from the group consisting of propylene glycol and glycerol.

2. The delivery system of claim 1, wherein the delivery system has an osmolarity measurement of about 5000 to about 7000 mOsm/liter.

3. The delivery system of claim 1, wherein the sugar derivative is present in amounts of about 30 to about 40% by weight.

4. The delivery system of claim 1, wherein the polyhydroxy alcohol is present in amounts of about 10% to about 15% by weight.

5. The delivery system of claim 1, wherein the system also includes one or more excipient selected from the group consisting of sweetening agents, colorants, surfactants, flavors, fragrances, pH modifiers, bulking agents, acidifiers and mixtures thereof.

6. The delivery system of claim 5, wherein the excipient is present in the system in an amount of about 0.01% to about 25% by weight of the high osmolarity aqueous system.

7. A liquid pharmaceutical delivery system having an osmolarity measurement of about 4000 to about 9000 mOsm/liter, which consists essentially of:
   a) from about 0.01% to about 5% by weight of one or more bitter tasting active material selected from the group consisting of analgesics, anti-inflammatories, antihistamines, antitussives, expectorants, decongestants, narcotics, antibiotics, bronchodilators, cardiovascular, central nervous system drugs, minerals, vitamins, metal salts and mixtures thereof; and
   b) a high osmolarity aqueous system having an osmolarity measurement of about 1500 to about 5000 mOsm/liter, consisting essentially of:
      (i) about 12% to about 30% by weight water;
      (ii) about 20% to about 45% by weight sugar derivative selected from the group consisting of sorbitol, mannitol, xylitol and mixtures thereof; and
      (iii) about 10% to about 15% by weight hydrogenated maltose syrup; and
      (iv) about 0% to about 35% by weight polyhydroxy alcohol selected from the group consisting of propylene glycol and glycerol.

8. A process for preparing a liquid pharmaceutical delivery system having an osmolarity measurement of about 4000 to about 9000 mOsm/liter, which comprises:
   a) preparing an aqueous phase consisting essentially of:
      (i) about 12% to about 30% by weight water;
      (ii) about 20% to about 45% by weight sugar derivative selected from the group consisting of sorbitol, mannitol, xylitol and mixtures thereof; and
      (iii) about 10% to about 15% by weight hydrogenated maltose syrup;
   b) blending the aqueous phase to form a high osmolarity homogeneous mixture of components having an osmolarity measurement of about 1500 to about 5000 mOsm/liter, said high osmolarity mixture consisting essentially of:
      (i) about 12% to about 30% by weight water;
      (ii) about 20% to about 45% by weight sugar derivative selected from the group consisting of sorbitol, mannitol, xylitol and mixtures thereof; and
      (iii) about 10% to about 15% by weight hydrogenated maltose syrup; and
      (iv) about 0% to about 35% by weight polyhydroxy alcohol selected from the group consisting of propylene glycol and glycerol;
   c) adding from about 0.01% to about 5% by weight of one or more bitter tasting active material selected from the group consisting of analgesics, anti-inflammatories, antihistamines, antitussives, expectorants, decongestants, narcotics, antibiotics, bronchodilators, cardiovascular, central nervous system drugs, minerals, vitamins, metal salts and mixtures thereof, to water and about 0% to about 35% by weight polyhydroxy alcohol;
   d) uniformly dispersing the one or more active material within the water to obtain a smooth dispersion or dissolution to form an active phase;
   e) blending the aqueous phase a) with the active phase d) to form a liquid pharmaceutical delivery system having an osmolarity measurement of about 4000 to about 9000 mOsm/liter; and
   f) recovering the same.

9. The process of claim 8, wherein the delivery system has an osmolarity measurement of about 5000 to about 7000 mOsm/liter.

10. The process of claim 8, wherein the sugar derivative is present in amounts of about 30 to about 40% by weight.

11. The process of claim 8, wherein the polyhydroxy alcohol is present in amounts of about 10% to about 15% by weight.

12. The process of claim 8, wherein the active material is a pharmaceutical drug.

13. The process of claim 8, wherein an excipient selected from the group consisting of sweetening agents, colorants, surfactants, flavors, fragrances, pH modifiers, bulking agents, acidifiers and mixtures thereof, is added to the mixture before the active phase is blended into the aqueous phase.

14. The process of claim 8, wherein an excipient selected from the group consisting of sweetening agents, colorants, surfactants, flavors, fragrances, pH modifiers, bulking agents, acidifiers and mixtures thereof, is added to the mixture while the active phase is blended into the aqueous phase.

15. The process of claim 8, wherein an excipient selected from the group consisting of sweetening agents, colorants, surfactants, flavors, fragrances, pH modifiers, bulking agents, acidifiers and mixtures thereof, is added to the mixture after the active phase is blended into the aqueous phase.

16. The process of claim 8, wherein an excipient is added to the mixture and is selected from the group consisting of sweetening agents, colorants, surfactants, flavors, fragrances, pH modifiers, bulking agents, acidifiers and mixtures thereof.

17. The process of claim 16, wherein the excipient is present in amounts up to 50% based on the weight of total components in the final product.

18. The process of claim 16, wherein the excipient is present in amounts from about 0.01% to about 25% by weight of the system.

19. The delivery system of claim 1, wherein the aqueous system has an osmolarity measurement of about 2000 to about 4000 mOsm/liter.

20. The process of claim 8, wherein the aqueous phase has an osmolarity measurement of about 2000 to about 4000 mOsm/liter.

21. The delivery system of claim 1, wherein the water is present in the amount of about 15% to about 25% by weight of the delivery system.

22. The process of claim 8, wherein the aqueous phase contains water in the amount of about 15% to about 25% by weight of the delivery system.

* * * * *